US012121466B2

United States Patent
Bean et al.

(10) Patent No.: US 12,121,466 B2
(45) Date of Patent: Oct. 22, 2024

(54) EXTERNAL ANKLE BRACE

(71) Applicant: TayCo Brace, Inc., South Bend, IN (US)

(72) Inventors: Michael W. Bean, South Bend, IN (US); Frederick John Ferlic, South Bend, IN (US)

(73) Assignee: TAYCO BRACE, INC., South Bend, IN (US)

( * ) Notice: Subject to any disclaimer, the term of this patent is extended or adjusted under 35 U.S.C. 154(b) by 0 days.

(21) Appl. No.: 17/986,290

(22) Filed: Nov. 14, 2022

(65) Prior Publication Data
US 2023/0071044 A1 Mar. 9, 2023

Related U.S. Application Data

(63) Continuation of application No. 17/345,103, filed on Jun. 11, 2021, now Pat. No. 11,497,644, which is a
(Continued)

(51) Int. Cl.
*A61F 5/01* (2006.01)
*A43B 7/20* (2006.01)

(52) U.S. Cl.
CPC .............. *A61F 5/0127* (2013.01); *A43B 7/20* (2013.01); *A61F 5/0195* (2013.01)

(58) Field of Classification Search
CPC .... A43B 7/20; A43B 5/00; A43B 5/18; A43B 5/185; A43B 7/00; A43B 7/14;
(Continued)

(56) References Cited

U.S. PATENT DOCUMENTS 1,692,896 A 11/1928 Hilgert
4,320,748 A * 3/1982 Racette ................ A61F 5/0585
602/23
(Continued)

OTHER PUBLICATIONS

Martin Alfuth et al., "Biomechanical Comparison of 3 Ankle Braces With and Without Free Rotation in the Sagittal Plane," Journal of Athletic Training, Oct. 2014, pp. 608-616, vol. 49, No. 5.
(Continued)

*Primary Examiner* — Caitlin A Carreiro
(74) *Attorney, Agent, or Firm* — Pilloff Passino & Cosenza LLP; Martin J. Cosenza

(57) ABSTRACT

An external ankle brace for restricting movement of an ankle in a first direction and permitting movement of the ankle in a second direction includes a rigid heel enclosure having a rear portion and a forward portion. A lateral upright extension is perpendicular to the rigid heel enclosure and is attached to the lateral sidewall. A medial upright extension is perpendicular to the rigid heel enclosure and is attached to the medial sidewall. At least a chosen one of the lateral and medial upright extensions is selectively pivotally attached to a corresponding lateral or medial sidewall and includes a pivot prevention feature configured to selectively prevent pivoting of the chosen one of the lateral and medial upright extensions with respect to the corresponding lateral or medial sidewall.

46 Claims, 9 Drawing Sheets

Related U.S. Application Data continuation of application No. 15/642,430, filed on Jul. 6, 2017, now Pat. No. 11,413,180, which is a continuation-in-part of application No. 15/074,339, filed on Mar. 18, 2016, now abandoned.

(60) Provisional application No. 62/135,823, filed on Mar. 20, 2015.

(58) Field of Classification Search
CPC .. A43B 7/142; A43B 7/18; A43B 7/19; A43B 7/24; A43B 7/32; A61F 5/00; A61F 5/0127; A61F 5/0195; A61F 5/0123; A61F 5/0102; A61F 5/01; A61F 5/0111; A61F 5/0113; A61F 2005/0132; A61F 2005/0146; A61F 2005/0137; A61F 2005/0148; A61F 2005/0165; A61F 2005/0167; A61H 3/00; A63B 23/08
USPC .......................... 602/16, 23, 27, 28, 65, 66
See application file for complete search history.

(56) References Cited

U.S. PATENT DOCUMENTS

| | | | |
|---|---|---|---|
| 4,510,927 A | 4/1985 | Peters | |
| 4,517,968 A | 5/1985 | Greene et al. | |
| 4,611,414 A | 9/1986 | Vogel | |
| 4,719,926 A | 1/1988 | Nelson | |
| 4,771,768 A | 9/1988 | Crispin | |
| 4,834,078 A | 5/1989 | Biedermann | |
| 4,977,891 A | 12/1990 | Grim | |
| 5,031,607 A | 7/1991 | Peters | |
| 5,069,202 A * | 12/1991 | Prock | A61F 5/0127 602/27 |
| 5,094,232 A | 3/1992 | Harris et al. | |
| 5,250,021 A | 10/1993 | Chang | |
| 5,429,588 A | 7/1995 | Young et al. | |
| 5,454,173 A * | 10/1995 | Falguere | A43B 5/0411 36/117.2 |
| 5,501,659 A | 3/1996 | Morris et al. | |
| 5,571,078 A | 11/1996 | Malewicz | |
| 5,676,642 A | 10/1997 | Peters | |
| 5,792,087 A | 8/1998 | Pringle | |
| 5,921,945 A | 7/1999 | Gray | |
| 5,992,057 A | 11/1999 | Monti | |
| 6,053,884 A | 4/2000 | Peters | |
| 6,267,742 B1 | 7/2001 | Krivosha et al. | |
| 6,299,587 B1 * | 10/2001 | Birmingham | A61F 5/0127 602/5 |
| 6,409,695 B1 | 6/2002 | Connelly | |
| 6,602,215 B1 | 8/2003 | Richie, Jr. | |
| 6,669,659 B2 * | 12/2003 | Dittmer | A61F 5/05841 602/5 |
| 6,689,081 B2 | 2/2004 | Bowman | |
| 6,860,864 B2 | 3/2005 | Meyer | |
| 7,127,836 B1 | 10/2006 | Jamison | |
| 7,624,519 B1 | 12/2009 | Thorne | |
| 7,785,283 B1 | 8/2010 | Bledsoe | |
| 8,221,341 B1 | 7/2012 | Al-Oboudi | |
| 8,540,655 B2 | 9/2013 | Franke et al. | |
| 9,259,343 B2 | 2/2016 | Newman | |
| 9,439,798 B2 | 9/2016 | Smith | |
| 9,603,736 B1 | 3/2017 | Buck | |
| 9,622,898 B1 | 4/2017 | Weber | |
| 9,844,455 B2 | 12/2017 | Bradshaw | |
| 10,271,982 B2 | 4/2019 | Volker | |
| 11,413,180 B2 | 8/2022 | Bean et al. | |
| 11,617,671 B2 | 4/2023 | Gildersleeve et al. | |
| 11,872,151 B2 | 1/2024 | Thor et al. | |
| 2001/0051780 A1 | 12/2001 | Birmingham | |
| 2004/0015112 A1 * | 1/2004 | Salutterback | A61F 5/0127 602/22 |
| 2004/0030275 A1 | 2/2004 | Morinaka | |
| 2004/0034316 A1 | 2/2004 | Castro | |
| 2004/0215123 A1 | 10/2004 | Slautterback et al. | |
| 2004/0225241 A1 | 11/2004 | Scheinberg et al. | |
| 2009/0287127 A1 | 11/2009 | Hu et al. | |
| 2010/0137770 A1 | 6/2010 | Ingmundarson et al. | |
| 2011/0173841 A1 | 7/2011 | McDuff | |
| 2012/0145167 A1 | 6/2012 | Davis | |
| 2013/0226059 A1 | 8/2013 | Morris | |
| 2014/0066829 A1 | 3/2014 | Drillio | |
| 2014/0257163 A1 | 9/2014 | Rittweger et al. | |
| 2015/0088044 A1 | 3/2015 | Walborn et al. | |
| 2015/0216703 A1 * | 8/2015 | Madden | A61F 5/0127 602/7 |
| 2015/0313743 A1 * | 11/2015 | Ostergard | A43C 1/00 602/27 |
| 2016/0029743 A1 | 2/2016 | Cavaliere et al. | |
| 2016/0235578 A1 * | 8/2016 | Romo | A61F 5/0127 |
| 2016/0270944 A1 | 9/2016 | Bean | |
| 2021/0298939 A1 | 9/2021 | Bean et al. | |

OTHER PUBLICATIONS

Patria A. Hume et al., "Effectiveness of External Ankle Support, Bracing and Taping in Rugby Union," Sports Medicine, May 1998, pp. 285-312, vol. 25, No. 5.
The Free Dictionary by Farlex, "plastically," https://www.thefreedictionary.com/plastically.
International Search Report and Written Opinion for PCT/US22/22018, mailed Jul. 25, 2022.
Merriam-Webster, "monolithic," https://www.merriam-webster.com/dictionary/monolithic.

* cited by examiner

EXTERNAL ANKLE BRACE

CROSS-REFERENCE TO RELATED APPLICATIONS

This application is a continuation of U.S. patent application Ser. No. 17/345,103, filed Jun. 11, 2021, which is a continuation of U.S. patent application Ser. No. 15/642,430, filed Jul. 6, 2017, now U.S. Pat. No. 11,413,180, which is a continuation-in-part of U.S. patent application Ser. No. 15/074,339, filed 18 Mar. 2016, which claims the benefit of U.S. Provisional Patent Application Ser. No. 62/135,823, which was filed on 20 Mar. 2015. Each of these applications is incorporated herein by reference, in its entirety, for all purposes.

TECHNICAL FIELD

The disclosure pertains generally to preventative and rehabilitative equipment, and more particularly to an ankle brace.

BACKGROUND

In the world of sports, ankle injuries are among the most common cause of lost playing time in a sporting career, with a typical ankle injury leaving the athlete out of competition for up to a month. Ankle sprains occur when there is a rapid shifting of weight from one direction to another. The force generated from the movement causes the foot to roll either inwards, which is known as inversion rotation; or outwards, which is known as eversion rotation. Both the inversion and eversion motion of the ankle cause the ligaments on the outside of the ankle to stretch or tear depending on the force that was generated during the movement.

Current braces vary from woven fabric that acts as a glove and wraps around the ankle, to rigid plastic uprights that are strapped around the ankle. The woven fabric braces typically are made of a thin fabric that envelope the ankle and are laced together to support the ankle from both inversion and eversion rotation. The main drawback with these types of braces is that the material lacks the resistance to prevent the ankle from rolling under intense forces. Further, fabric braces also have to be worn within the shoe, which causes the shoe to fit tighter or, in some cases, forces the user to move up a shoe size in order to wear the brace. In terms of the rigid uprights braces, these braces are typically much heavier than the fabric braces and also much larger. Fitting a rigid brace into a tight shoe almost never works, which forces the user to move up to the next shoe size to accommodate for the bulkiness of the brace. When the user moves up a shoe size, the shoe is no longer sized correctly for the foot and thus loses a portion of its intended use and purpose. These braces leave the user at risk for further injury because either the brace isn't strong enough to support the ankle or the shoe isn't fitted properly to the foot.

SUMMARY

In an embodiment, an external ankle brace for restricting movement of an ankle in a first direction and permitting movement of the ankle in a second direction is provided. The external ankle brace is disposed on the exterior of a shoe and the shoe has a heel portion, a sole, and oppositely disposed sides. A rigid heel enclosure has a rear portion and a forward portion. The rear portion is for receiving the heel of the shoe. The forward portion has a medial sidewall and a lateral sidewall for surrounding the sides of the shoe. A lateral upright extension is perpendicular to the rigid heel enclosure and is attached to the lateral sidewall. A medial upright extension is perpendicular to the rigid heel enclosure and is attached to the medial sidewall. A lower fastening system comprises at least one connecting strap for connecting the lateral sidewall to the medial sidewall underneath the sole of the shoe. An upper fastening system comprises at least one connecting strap for removably connecting the lateral sidewall to the medial sidewall across the top of the shoe. At least a chosen one of the lateral and medial upright extensions is selectively pivotally attached to a corresponding lateral or medial sidewall. The chosen one of the lateral and medial upright extensions includes a pivot prevention feature configured to selectively prevent pivoting of the chosen one of the lateral and medial upright extensions with respect to the corresponding lateral or medial sidewall.

BRIEF DESCRIPTION OF THE DRAWINGS

These and other features, aspects, and advantages of the present disclosure will become better understood when the following detailed description is read with reference to the accompanying drawings in which like numerals are used to indicate like structure throughout the various figures.

DETAILED DESCRIPTION

Figure 1:
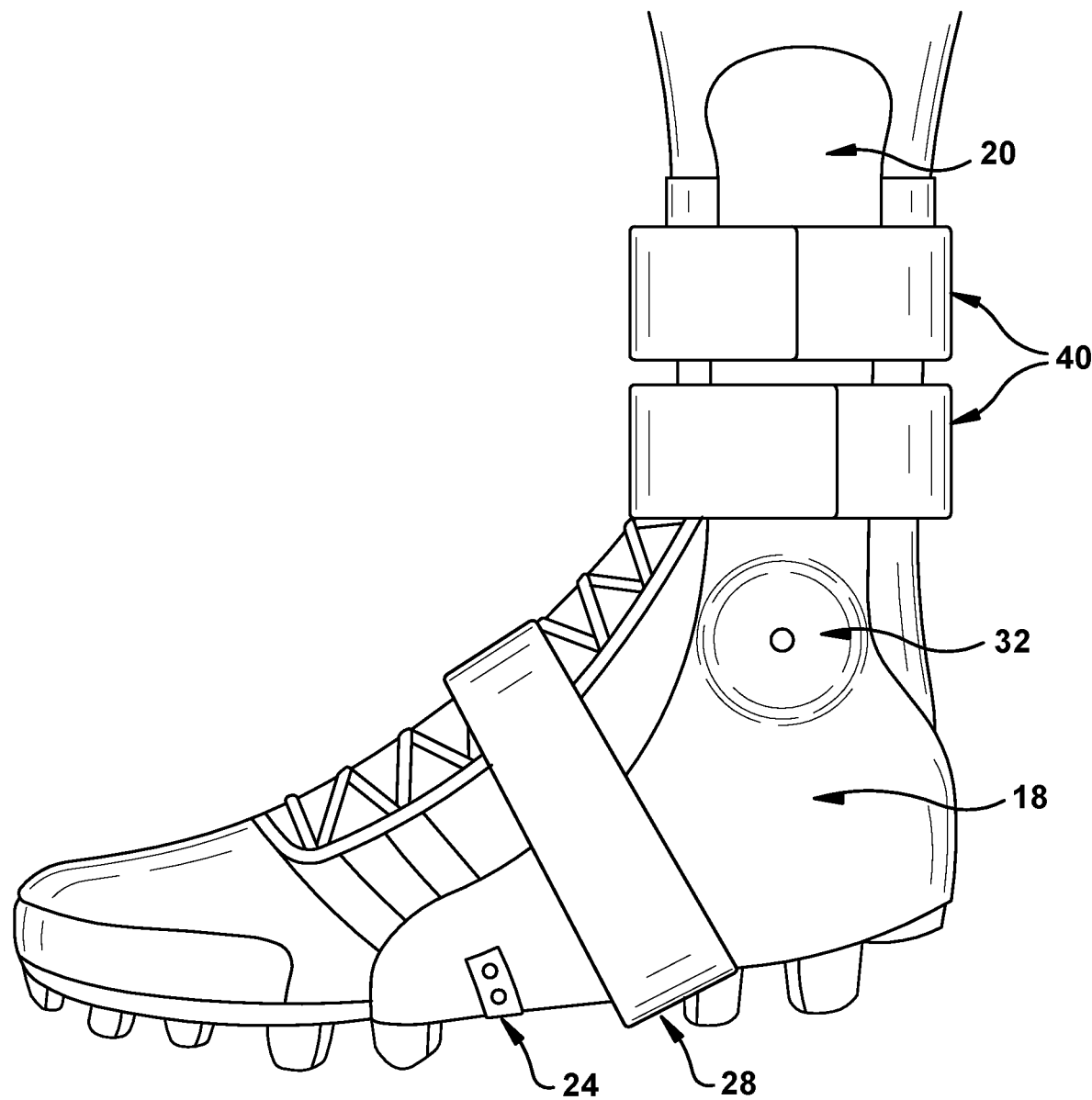
FIG. 1 is a lateral side view showing a first embodiment of the external ankle brace with an athletic shoe.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure.

The invention comprises, consists of, or consists essentially of the following features, in any combination.

Ankle injuries are among the most common cause of lost playing time in a sporting career and although there are current preventative solutions, those current braces leave the user at risk for further injury because either the brace isn't strong enough to support the ankle or the shoe isn't fitted properly to the foot since "inside the shoe" braces tend to force the user to use a bigger shoe size. The present disclosure provides a rigid support and a much faster application time, all without compromising the fit of the shoe.

The present disclosure relates to an external ankle brace that is adapted to fit around a shoe to prevent and minimize injury to an ankle. The shoe having a heel portion, a sole, and oppositely disposed sides. The interaction between the external ankle brace and the shoe can be seen in FIG. 1.

Figure 2:
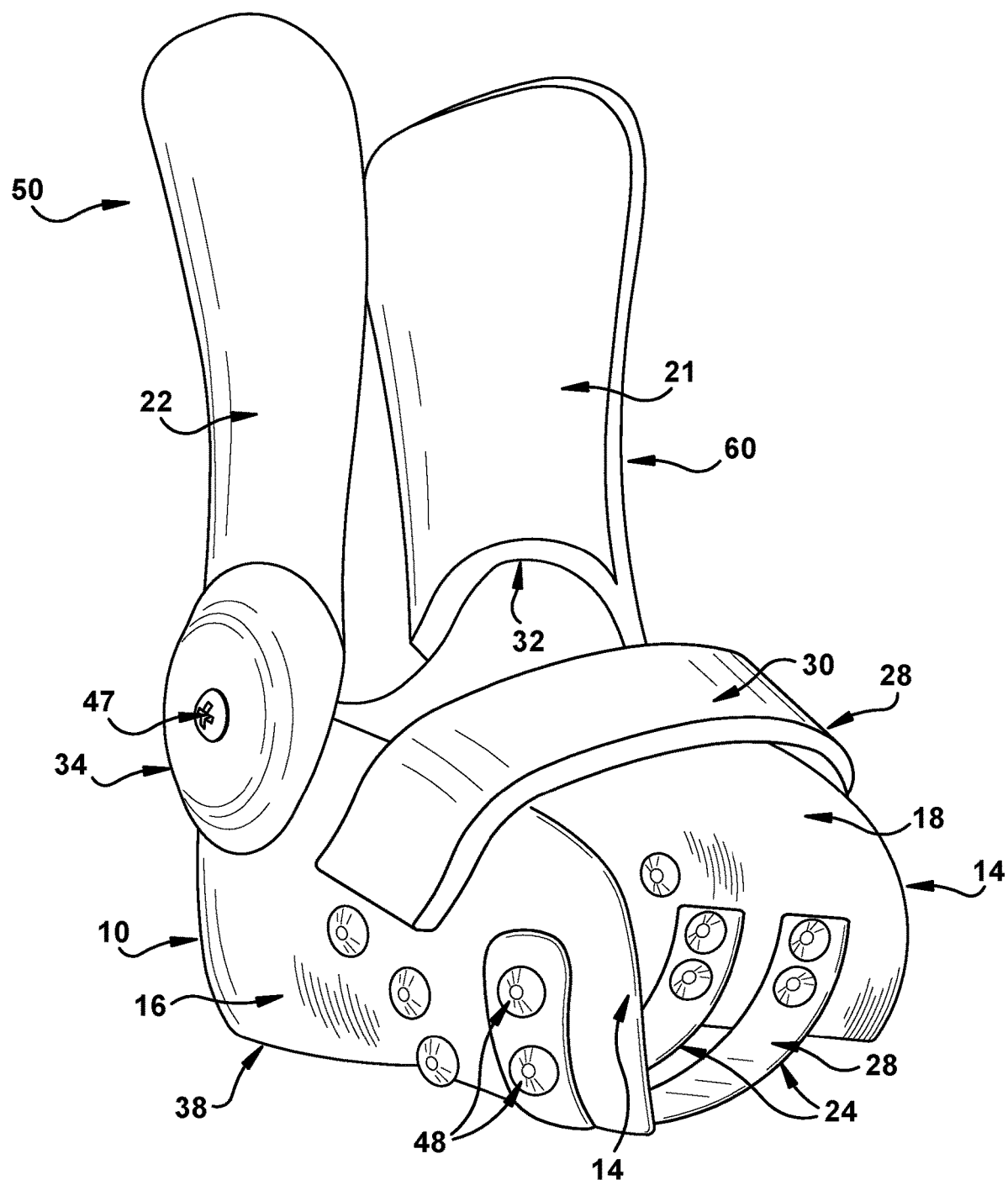
FIG. 2 is a perspective view of the external ankle brace of FIG. 1 from the medial side.

The external ankle brace of the present disclosure is generally indicated at 50 in FIG. 2. The external ankle brace 50 includes a rigid heel enclosure 10, a lateral upright extension 20, a medial upright extension 22, a lower fastening system 24, and an upper fastening system 28.

Figure 3:
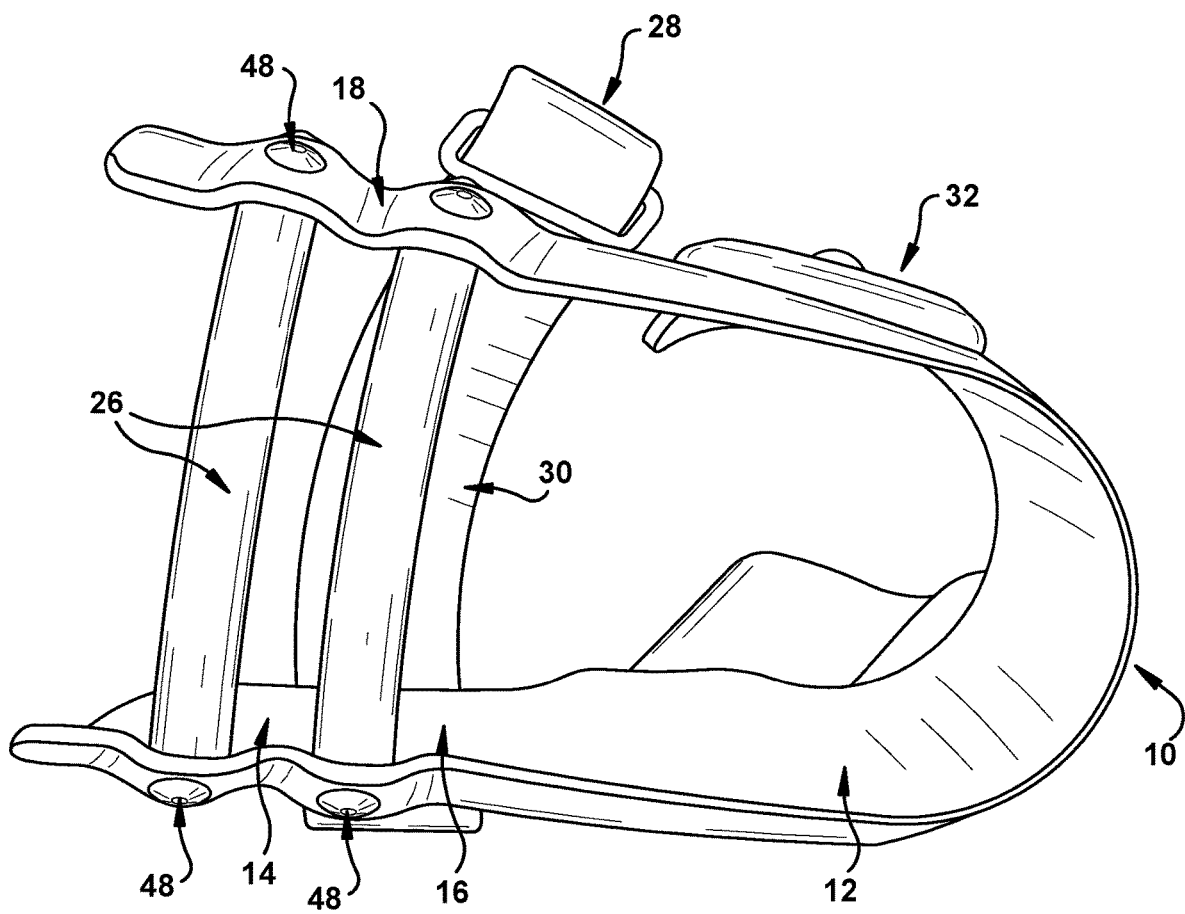
FIG. 3 is a perspective view showing the underside of the external ankle brace of FIG. 1.

The rigid heel enclosure 10 has a rear portion 12 (FIG. 3), for receiving the heel of the shoe, and a forward portion 14, for surrounding the sides of the shoe. The heel enclosure 10 may be made from rigid plastic pieces or any other suitable material. The forward portion 14 further includes a medial sidewall 16 and a lateral sidewall 18. The rigid heel enclosure 10 also has an upper end 36 (FIG. 2) for receiving the upright extensions 20 and 22, and a lower end 38 for surrounding the bottom of the shoe.

Figure 4:
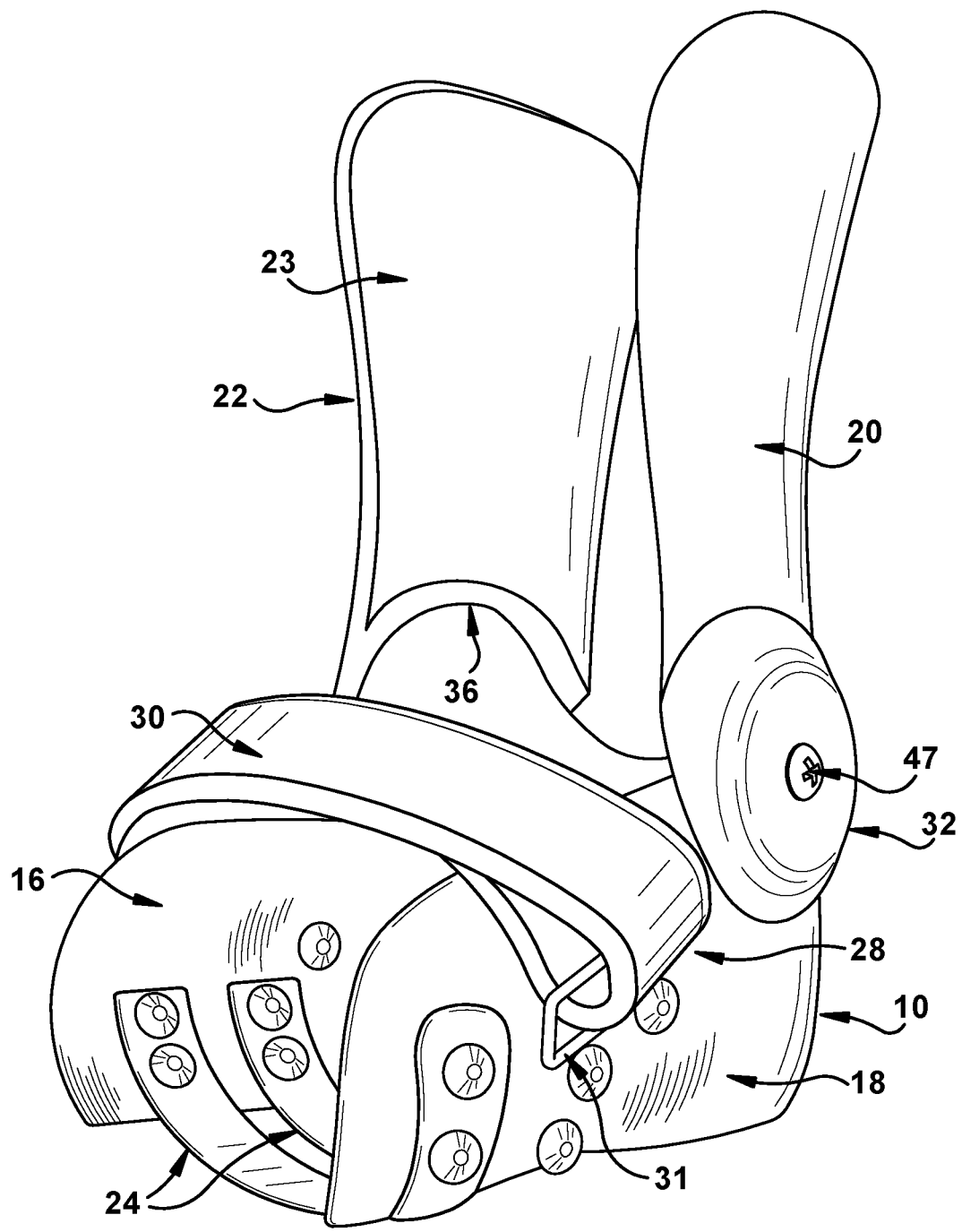
FIG. 4 is a perspective view of the external ankle brace of FIG. 1 from the lateral side.
Figure 5:
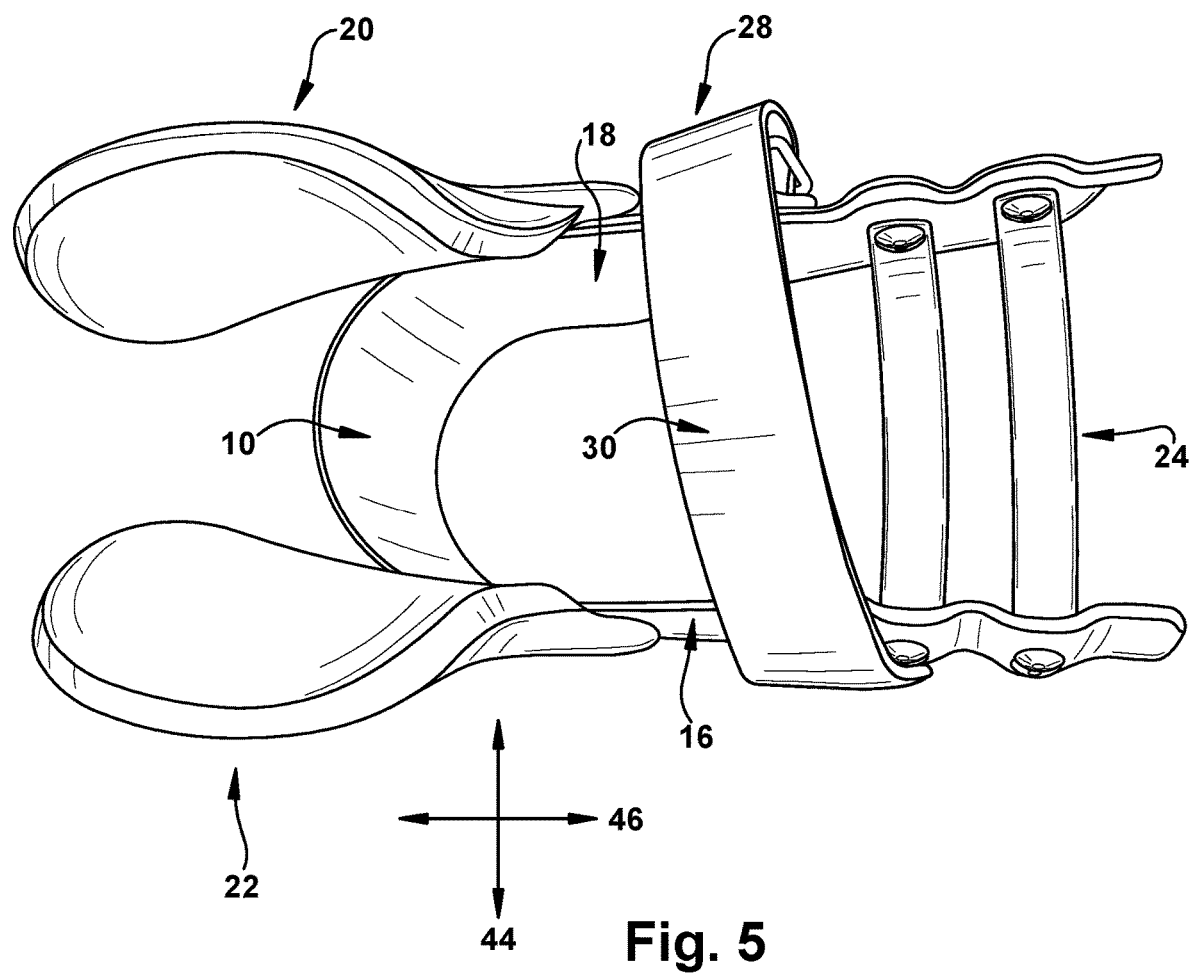
FIG. 5 is a top view of the external ankle brace of FIG. 1.
Figure 6:
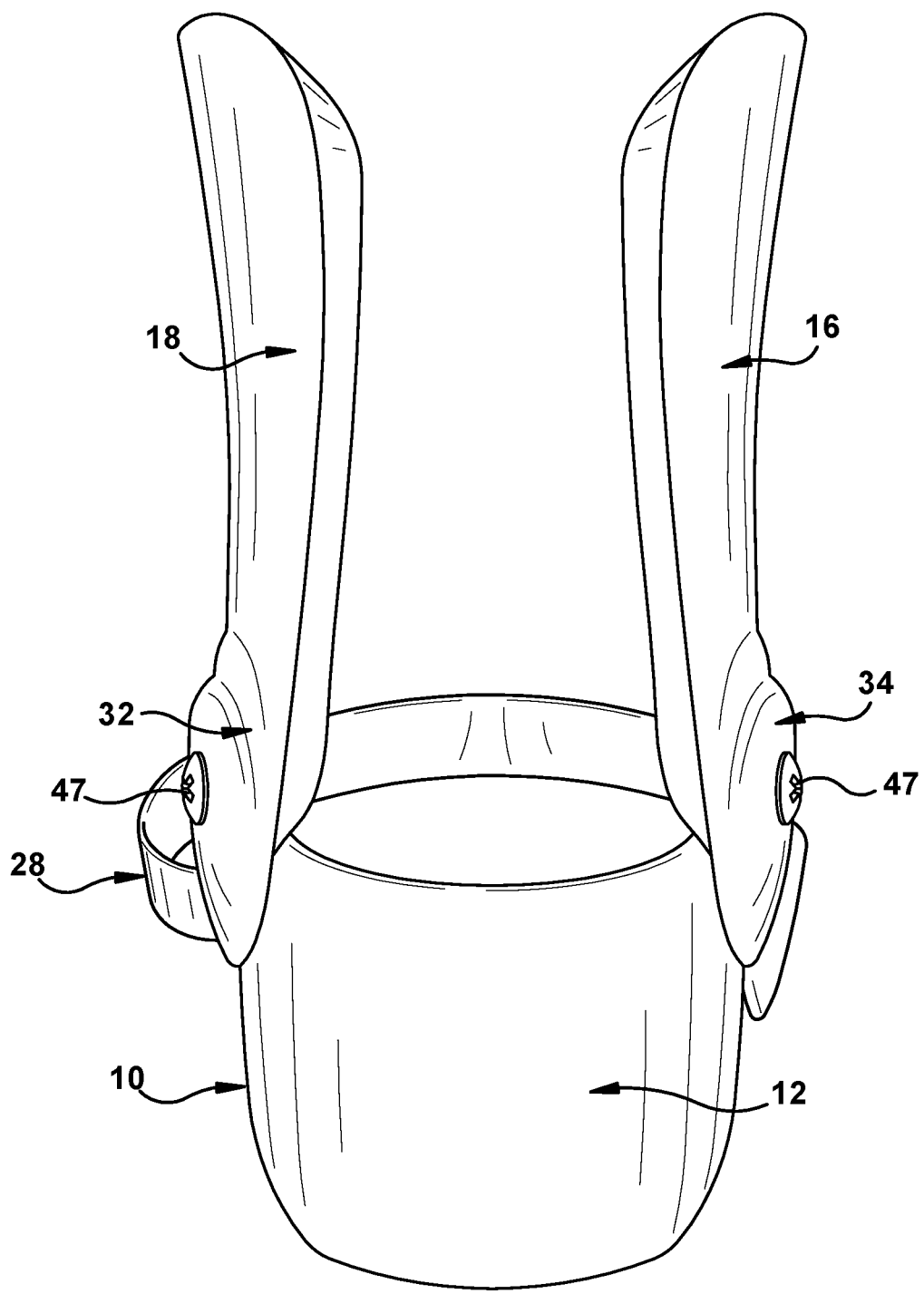
FIG. 6 is a rear view of the external ankle brace of FIG. 1.

The lateral upright extension 20 is oriented generally perpendicular to the rigid heel enclosure 10 and is pivotally attached to the lateral sidewall 18 at the upper end 36 by a lateral ankle joint 32 (FIG. 4). The joint allows the lateral upright extension 20 to rotate during motion giving the external ankle brace a less restrictive feel compared to previous braces. The lateral upright extension 20 may be made from plastic or any other suitable material. The lateral ankle joint 32 includes a fastener 47 and allows the lateral upright extension 20 to rotate relative to the lateral sidewall 18. Although the current embodiment uses a screw as the fastener 47, one having ordinary skill in the art will appreciate that a pivot hinge, hex nut, revolving joint, or any other suitable member of the type commonly known in the art could be used to allow the joint to pivot. As shown in FIG. 5, the lateral upright extension 20 has a concave shape for increased comfort for the user. The lateral upright extension 20 can also include foam padding on the interior side 21 (FIG. 2) of the lateral upright extension 20 to increase comfort and to allow a better fit for the user.

The medial upright extension 22 is perpendicular to the rigid heel enclosure 10 and is pivotally attached to the medial sidewall 16 at the upper end 36 by a medial ankle joint 34. The medial upright extension 22 may be made of rigid plastic or any other suitable material. The medial ankle joint 34 has a fastener 47 and allows the medial upright extension 22 to rotate relative to the medial sidewall 16. To adjust for anatomical positioning of the ankle, the medial ankle joint 34 is positioned closer to the upper end 36 than the position of the lateral ankle joint 32. Although the current embodiment uses a screw as the fastener 47, one having ordinary skill in the art will appreciate that a pivot hinge, hex nut, revolving joint, or any other suitable member of the type commonly known in the art could be used to allow the joint to pivot. As shown in FIG. 5, the medial upright extension 22 has a concave shape for increased comfort for the user. The medial upright extension 22 can also include foam padding on the interior side 23 (FIG. 4) of the medial upright extension to increase comfort and to allow a better fit for the user.

The lower fastening system 24 has at least one connecting strap 26 and at least one strap fastener 48 for connecting the lateral sidewall 18 to the medial sidewall 16 (FIG. 2) while passing underneath the sole of the shoe. Although the current embodiment uses a rubber strap 26, one having ordinary skill in the art would appreciate that plastic, nylon, or any other suitable strap type that is commonly known in the art could be used. Similarly, although the current embodiment uses rivets 48 to fasten the straps to each of the lateral and medial sidewalls 18 and 16 respectively, any other fastener could be used.

The upper fastening system 28 has at least one connecting strap 30 and at least one strap fastener 48 (FIG. 4) for removably connecting the lateral sidewall 18 to the medial sidewall 16 while passing over the top of the shoe. The upper fastening system further includes a D-ring 31 which is fixed on the lateral sidewall. The Velcro strap 30 is fixed to the medial sidewall and is looped through the D-ring 31 and overlaps back onto the strap 30. This allows for an adjustable fastening system to accommodate various sizes without compromising support. Although the current embodiment uses a Velcro strap 30 to removably connect the sidewalls 16 and 18, one having ordinary skill in the art would appreciate that any kind of removable and adjustable strap can be used. Similarly, although the current embodiment only uses one connecting strap 30, any number of straps can be used to removably connect the sidewalls 16 and 18 over the top of the shoe.

As shown in FIG. 5, the external ankle brace 50 restricts movement of the ankle in the first directions indicated by arrows 44 and permits ankle movement in the second directions indicated by arrows 46.

Another embodiment (not shown) could include an upright fastening system 40 (FIG. 1), which would have at least one connecting strap for removably connecting the lateral upright extension 20 to the medial upright extension 22 above the ankle. This connecting strap could be Velcro or any other type of strap that would allow for an adjustable and removable connection.

Figure 7:
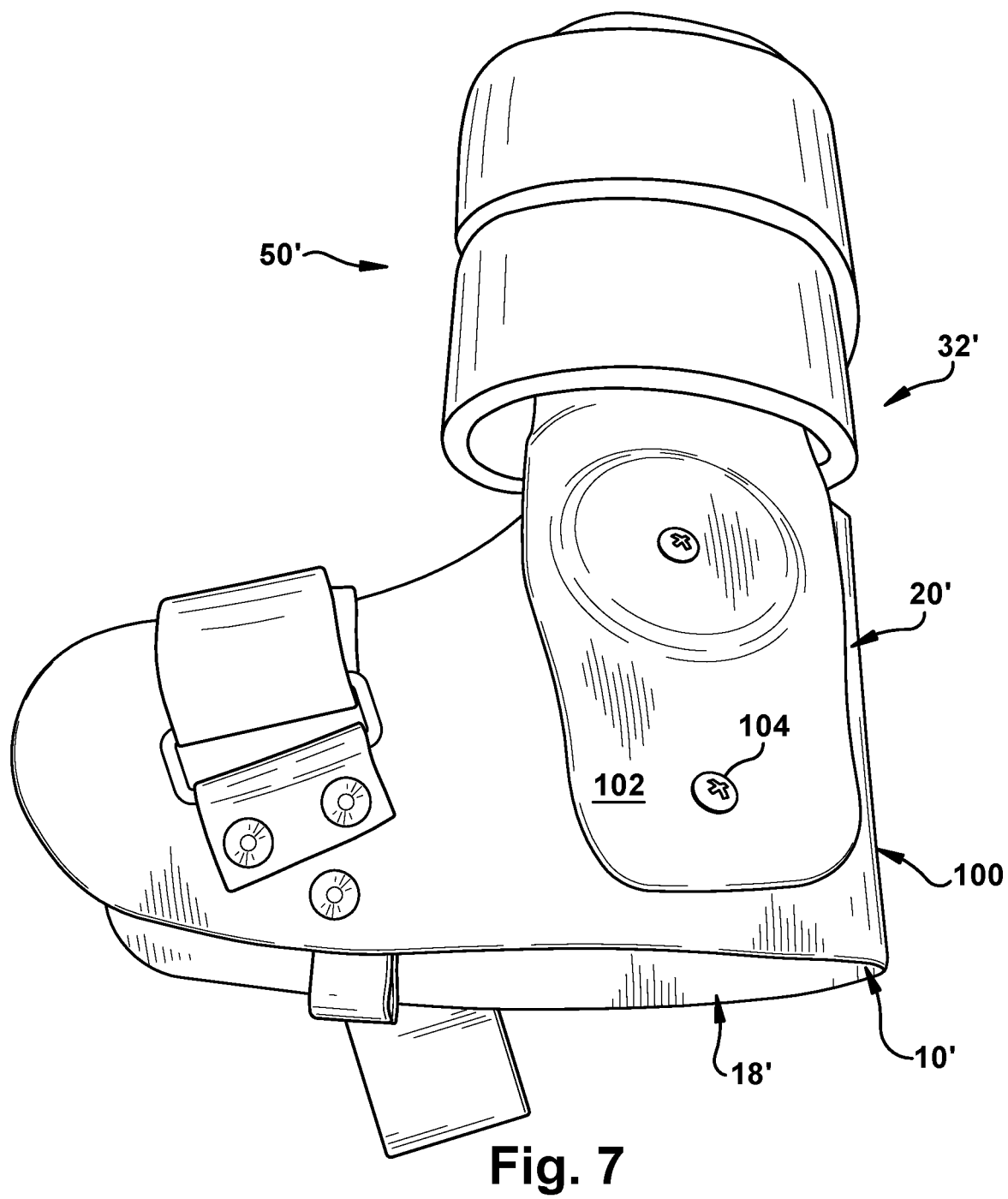
FIG. 7 is a lateral side view depicting a second embodiment of the external ankle brace.
Figure 8:
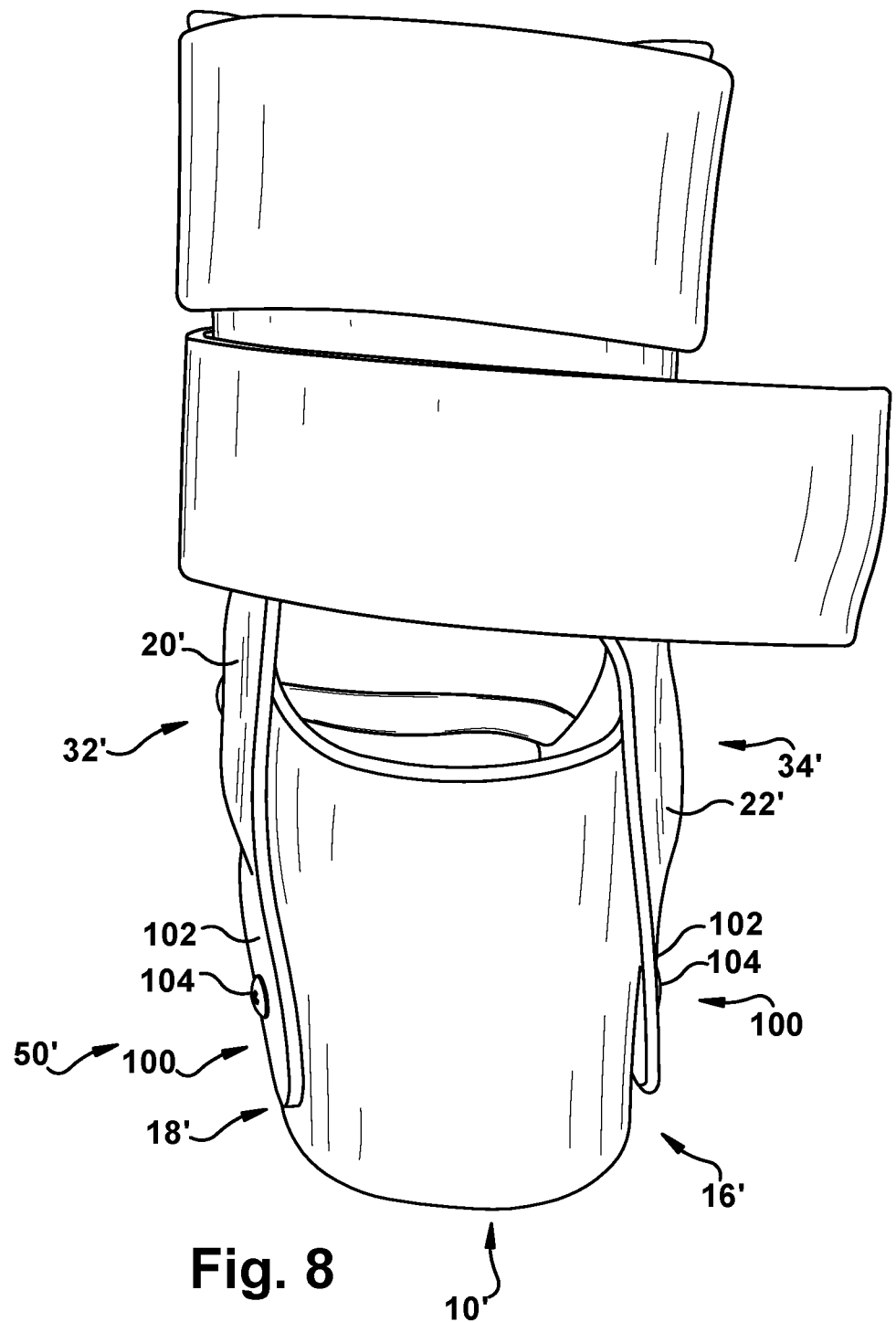
FIG. 8 is a rear view of the embodiment of FIG. 7.
Figure 9:
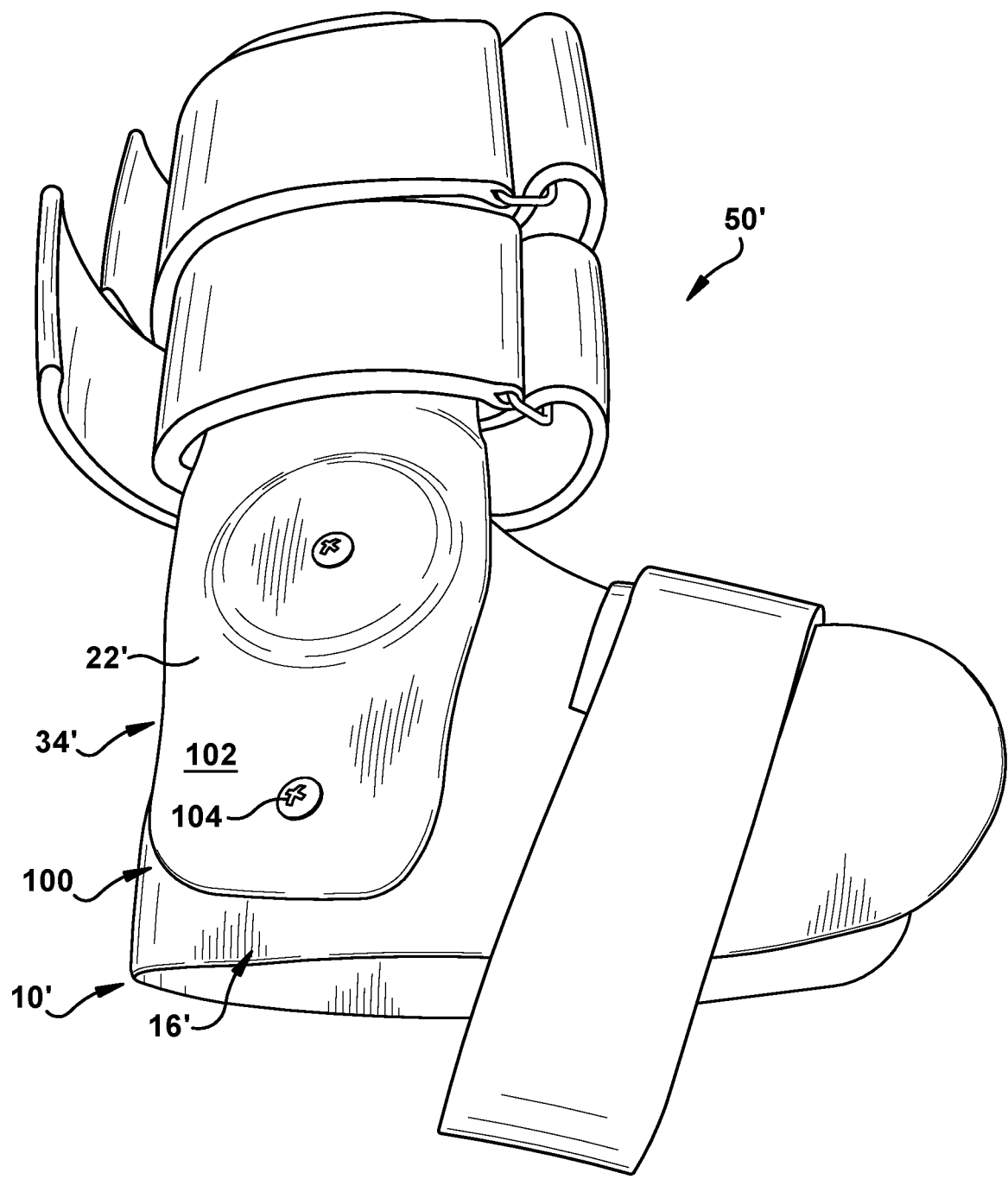
FIG. 9 is a medial side view of the embodiment of FIG. 7.

FIGS. 7-9 depict an external ankle brace 50' of a second embodiment. The external ankle brace 50' of FIGS. 7-9 is similar to the external ankle brace 50 of FIGS. 1-6 and therefore, structures of FIGS. 7-9 that are the same as or similar to those described with reference to FIGS. 1-6 have the same reference numbers with the addition of a "prime" mark. Description of common elements and operation similar to those in the previously described first embodiment will not be repeated with respect to the second embodiment.

In FIGS. 7-9, the external ankle brace 50' of the second embodiment, in contrast to that of the first embodiment, is configured with lateral and/or medial ankle joints 32' and 34' that selectively pivotally connect their corresponding lateral and/or medial upright extensions 20' and 22' to the corresponding lateral and/or medial sidewalls 18' and 16' and thus selectively allow the lateral and medial upright extensions 20' and 22' to move in the second direction relative to the heel enclosure 10'. Stated differently, the external ankle brace 50' of the second embodiment allows a user, or an associated medical professional, to "lock" pivoting of the external ankle brace 50' as desired, either for an entirety of the use/wear, or for a predetermined period of time during use of the external ankle brace 50' by the user. For example, the external ankle brace 50' could be prevented from the above-described pivotal movement in the second direction during an initial phase of healing of an injury, and then the external ankle brace 50' could be released to allow pivotal movement in the second direction once it is determined that such may be beneficial, or at least not detrimental, to the healing of that injury.

In order to provide such selective pivotal movement, the external ankle brace 50' of the second embodiment could include at least a chosen one (and/or both) of the lateral and medial upright extensions 20' and 22' which is selectively pivotally attached to a corresponding lateral or medial sidewall 18' and 16'. The chosen lateral and/or medial upright extensions 20' and 22' may include a pivot prevention feature 100 which is configured to selectively prevent pivoting of the chosen one of the lateral and medial upright extensions 20' and 22' with respect to the corresponding lateral or medial sidewall 18' and 16'.

As shown in FIGS. 7-9, the pivot prevention feature 100 may include a "tongue" or extension 102 from the corresponding lateral and/or medial upright extensions 20' and 22' downward toward the heel enclosure 10'. That extension 102 is then selectively secured to the corresponding lateral or medial sidewall 18' and 16' through use of a fastener 104, such as, but not limited to, the depicted screws. The combination of the extension 102, the fastener 104, and the lateral and medial sidewalls 18' and 16' then serves to inhibit or prevent pivoting or rotation of the lateral and/or medial upright extensions 20' and 22' with respect to the lateral or medial sidewalls 18' and 16'. While the extension 102 is shown as reaching substantially downward from a corresponding lateral and/or medial upright extensions 20' and 22' in FIGS. 7-9, it is also contemplated that the extension 102 could be oriented differently with respect to the remaining portions of the corresponding lateral and/or medial upright extensions 20' and 22', or the fastener 104 could be associated with the corresponding lateral and/or medial upright extensions 20' and 22' without the use of an extension 102, such as by extending the lateral and medial sidewalls 18' and 16' upward to allow placement of the fastener 104 above the lateral and/or medial ankle joints 32' and 34'.

The pivot prevention feature 100 depicted in the FIGS. is just one nonlimiting example, in fact, of any of a number of suitable mechanisms which can help with selectively inhibiting pivoting or rotation of the lateral and/or medial upright extensions 20' and 22' with respect to the lateral or medial sidewalls 18' and 16'. Other suitable mechanisms could include latches, frictional fit features, hooks, clips, straps, or any other structure which may be helpful in allowing selective prevention of at least some degree of rotation of the lateral and/or medial upright extensions 20' and 22' with respect to the lateral or medial sidewalls 18' and 16'. One of ordinary skill in the art will be able to provide a suitable pivot prevention mechanism 100 for a particular use environment of the external ankle brace 50'.

Embodiments can minimize ankle inversion and eversion during physical activity and/or minimize ankle medial and later rotation during physical activity and/or minimize ankle plantar flexion and dorsiflexion during physical activity and/or provide stability to the mid foot in limiting pronation and supination of the foot.

Embodiments can include a foot/ankle orthotic that includes a lateral sidewall, a medial sidewall, a heel enclosed backing connecting the sidewalls, a lateral upright extension, a medial upright extension and a bottom strapping system connecting sidewalls. The lateral and medial upright extensions are attached to the sidewalls with an overlapping ankle joint off-set to accommodate for medial and lateral malleolus anatomical positioning. The lateral sidewall coincides with the outer or exterior portion of the foot/ankle and the medial sidewall coincides with the inner portion of the foot/ankle. The lateral upright extension coincides with the outer or exterior portion of the lower leg and the medial upright extension coincides with the inner portion of the lower leg. Lateral and medial extension walls are configured to rise above the ankle of the wearer of the orthotic by approximately 8-9 inches (from the bottom of the hinge to the top of the extension walls). When donned by the wearer, lateral and medial side walls also partially wrap over the top or dorsum of the foot leaving a gap of approximately 3 to 4 inches between the sidewalls. The width of the medial and lateral upright extensions is approximately 3-4 inches wide.

A feature of an embodiment is to have the securing mechanism include a hook and loop strap across the dorsal (top) of the foot. This Velcro securing strap is riveted to the in place on both the medial and later side walls. A D ring is utilized on the lateral fixation in which the Velcro strap can be fed through and secured back upon itself. The lateral and medial upright extensions are secured by two removable Velcro straps and D rings. Male component Velcro is adhesively attached to each upright and the female component Velcro strap can connect to the uprights are desired positions for appropriate fitting. As an option, the brace may also be applied with various types of athletic adhesive tape in conjunction with or instead of the Velcro strapping and D ring system.

Another feature of an embodiment is an overlapping ankle joint hinge to allow the ankle to move freely through plantar flexion and dorsiflexion. The overlapping ankle joint is located on the medial and lateral aspects of the gauntlet where the medial and lateral side bodies attach with the medial and lateral uprights respectively. The ankle joint hinge components are off set to produce a more anatomically correct gauntlet for a more fluid mobility.

Foam padding (approximately X inch) is attached to the inside of both the medial and lateral uprights to provide additional comfort and protection for the wearer. The gauntlet is sized so that one size can fit multiple size shoes. A separate gauntlet is needed to accommodate both right and left ankles.

A sheet of vacuum formable thermoplastic large enough to cover the entire mold is cut and placed in an oven to be heated to a formable temperature. These are several types and thicknesses of plastic that may be used for this fabrication including orthotic grade polypropylene, polyethylene, and copolymer.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

What is claimed is:

1. An external ankle brace for restricting movement of an ankle in a first direction and permitting movement of the ankle in a second direction, wherein said external ankle brace is disposed on the exterior of a shoe and the shoe has a heel portion, a sole, and oppositely disposed sides, comprising:
    a rigid heel enclosure having a rear portion and a forward portion, said rear portion for receiving the heel of the shoe, said forward portion having a medial sidewall and a lateral sidewall for surrounding the sides of the shoe, the medial and lateral sidewalls being cantilevered from the rear portion of the rigid heel enclosure, the medial and lateral sidewalls each being configured to extend from the heel portion of the shoe in a longitudinal direction beyond a talus of a wearer's foot and toward the toes, each of the medial and lateral sidewalls being at least partially located adjacent to an instep area of a corresponding medial or lateral side of the shoe;
    a lateral upright extension movable to and from a perpendicular orientation relative to said rigid heel enclosure and pivotally attached to said lateral sidewall;
    a medial upright extension movable to and from a perpendicular orientation relative to said rigid heel enclosure and pivotally attached to said medial sidewall;
    a lower fastening system comprising at least one connecting strap for connecting said lateral sidewall to said medial sidewall underneath the sole of the shoe forward of the talus of the wearer's foot, the lower fastening system being the only structure connecting the lateral and medial sidewalls underneath the sole of the shoe such that a portion of the sole of the shoe configured to be underneath a heel of the wearer's foot is exposed to ambient space beneath the shoe; and
    an upper fastening system comprising at least one connecting strap for removably connecting said lateral sidewall to said medial sidewall across the top of the shoe, the at least one connecting strap being fixed to at least one of the medial or lateral sidewalls,
    wherein, when viewed from the bottom, the rigid heel enclosure forms a U-shaped body, and
    wherein the external ankle brace is configured so that at least a chosen one of the lateral or medial upright extensions is selectively pivotally attached to a corresponding lateral or medial sidewall, the chosen one of the lateral or medial upright extensions including a pivot prevention feature configured to selectively prevent pivoting of the chosen one of the lateral or medial upright extensions with respect to the corresponding lateral or medial sidewall and thus maintain the chosen one of the lateral or medial upright extensions in a vertical orientation substantially perpendicular to the longitudinal direction.

2. The external ankle brace as set forth in claim 1, further including a lateral ankle joint that selectively pivotally connects said lateral upright extension to said lateral sidewall and selectively allows said lateral upright extension to move in the second direction relative to said heel enclosure.

3. The external ankle brace as set forth in claim 2, wherein said lateral ankle joint in combination with said lateral upright extension and said heel enclosure are configured to prevent movement of the ankle in the first direction.

4. The external ankle brace as set forth in claim 3, further comprising an upright fastening system comprising at least one connecting strap for removably connecting said lateral upright extension to said medial upright extension above the ankle.

5. The external ankle brace as set forth in claim 3, further including a medial ankle joint that pivotally connects said medial upright extension to said medial sidewall and allows said medial upright extension to move in the second direction relative to said heel enclosure.

6. The external ankle brace as set forth in claim 2, further including a medial ankle joint that selectively pivotally connects said medial upright extension to said medial sidewall and selectively allows said medial upright extension to move in the second direction relative to said heel enclosure.

7. The external ankle brace as set forth in claim 6, wherein said medial ankle joint in combination with said medial upright extension and said heel enclosure prevent movement in the first direction.

8. The external ankle brace as set forth in claim 6, wherein said heel enclosure further includes oppositely disposed upper and lower ends, where said medial ankle joint is positioned closer to said upper end than the position of said lateral ankle joint.

9. The external ankle brace as set forth in claim 6, wherein said lateral ankle joint in combination with said lateral upright extension and said heel enclosure and said medial ankle joint in combination with said medial upright extension and said heel enclosure prevent movement in the first direction.

10. The external ankle brace as set forth in claim 1, further comprising an upright fastening system comprising at least one connecting strap for removably connecting said lateral upright extension to said medial upright extension above the ankle.

11. The external ankle brace as set forth in claim 1, wherein:
the medial sidewall is completely inside the medial upright extension.

12. The external ankle brace as set forth in claim 1, wherein:
the external ankle brace is configured so that respective portions of the medial and lateral sidewalls extend in a manner that the wearer's foot, when the external ankle brace is worn by the wearer, is located directly between the medial and lateral sidewalls.

13. The external ankle brace as set forth in claim 1, wherein:
a bottom surface of the heel enclosure continuously extends from a tip of a distal portion of the lateral sidewall, to a proximal portion of the lateral sidewall, to the rear portion, to a proximal portion of the medial sidewall and then to a tip of a distal portion of the medial sidewall.

14. The external ankle brace as set forth in claim 1, wherein:
the lateral sidewall smoothly transitions from a distal portion of the lateral sidewall to a location on a proximal portion of the lateral sidewall above an uppermost portion of the lateral sidewall midway between a front and a rear of the brace when viewed from a side of the brace.

15. The external ankle brace as set forth in claim 1, wherein:
the medial and lateral sidewalls have a silhouette of a shoe when viewed from a side of the brace.

16. The external ankle brace as set forth in claim 1, wherein:
the external ankle brace is configured so that respective portions of the medial and lateral sidewalls extend in a manner that the wearer's foot, when the external ankle brace is worn by the wearer, is located directly between the medial and lateral sidewalls and the medial and lateral sidewalls are configured to extend from the heel portion of the shoe in the longitudinal direction to respective locations beyond the talus of the wearer's foot and toward the toes with the foot directly located in between the respective locations.

17. The external ankle brace as set forth in claim 1, wherein the heel enclosure is made of plastic and is a monolithic body.

18. The external ankle brace as set forth in claim 1, wherein the rigid heel enclosure is configured so that one size fits multiple size shoes.

19. The external ankle brace as set forth in claim 1, wherein:
the external ankle brace is configured so that respective portions of the medial and lateral sidewalls extend in a manner that the wearer's foot, when the external ankle brace is worn by the wearer, is located indirectly between the medial and lateral sidewalls.

20. The external ankle brace as set forth in claim 1, wherein the medial and lateral sidewalls are means for surrounding the oppositely disposed sides of the shoe.

21. The external ankle brace as set forth in claim 1, wherein the external ankle brace is configured for one of a right or left ankle, and a separate different external ankle brace is needed for the other of the right or left ankle.

22. An external ankle brace, comprising:
a lower leg section configured to interface with a leg of a human at a lower leg thereof; and
a foot section configured to interface with a shoe worn on a foot of the human at locations where the foot of the human is located, wherein
the external ankle brace is configured to restrict movement of an ankle of the human in a first direction and permit movement of the ankle in a second direction, wherein said external ankle brace is configured to be disposed on the exterior of the shoe of the human, the shoe having a heel portion, a sole, and a toe section, the heel portion being at a rear of the shoe, and the toe section being at a front of the shoe,
the foot section is established by a portion that includes a first subportion, a second subportion and a third subportion, the first subportion of the foot section being configured to receive the rear of the shoe, the second subportion of the foot section extending away from the first subportion and configured to be on a medial side of the foot when the brace is worn by the human, the third subportion of the foot section extending away from the first subportion and configured to be on a lateral side of the foot when the brace is worn by the human,
the lower leg section includes a lateral upright extension that includes a portion that extends upward away from the foot section, the lateral upright extension being rotationally attached to the foot section,
the lower leg section includes a medial upright extension that includes a portion that extends upward away from the foot section, the medial upright extension being rotationally attached to the foot section,
the external ankle brace further includes:
a foot fastening arrangement comprising at least one connecting strap connecting said second subportion to said third subportion; and
a lower leg section fastening system comprising at least one connecting strap connecting said portion of said medial upright extension that extends upwardly away from the foot section with said portion of said lateral upright extension that extends upwardly away from the foot section, and the at least one connecting strap of the foot fastening arrangement connects the second subportion to the third subportion underneath the sole of the shoe, and the foot fastening arrangement comprises a second connecting strap connecting the second subportion to the third subportion across the top of the shoe.

23. The external ankle brace as set forth in claim 22, further including an ankle joint that selectively pivotally connects said upright extension to said foot section and selectively allows said upright extension to move in the second direction relative to said foot section.

24. The external ankle brace as set forth in claim 23, wherein said first subportion of said foot section includes oppositely disposed upper and lower ends, where said medial ankle joint is positioned closer to said upper end than the position of said lateral ankle joint.

25. The external ankle brace as set forth in claim 22, wherein the external ankle brace is configured permit movement of the ankle in a third direction opposite the second direction, the second direction and third direction normal to the first direction.

26. The external ankle brace as set forth in claim 25, wherein the external ankle brace is configured to restrict movement of the ankle in a fourth direction opposite the first direction.

27. The external ankle brace as set forth in claim 22, further including an ankle joint that enables the rotational attachment of the medial upright extension that selectively pivotally connects said medial upright extension to said lower section and selectively allows said upright extension to move in the second direction relative to said foot section.

28. The external ankle brace as set forth in claim 22, wherein:
the shoe is a laced shoe, and is located in the brace and located directly between the second subportion and the third subportion, and the first subportion is plastic and encloses the heel portion of the shoe.

29. The external ankle brace as set forth in claim 22, wherein:
the shoe is an athletic shoe and is located in the brace and located directly between the medial and lateral sidewalls; and
the second subportion of the foot section and the third subportion of the foot section are contoured with respective opposite sides of the shoe.

30. The external ankle brace as set forth in claim 22, wherein the second direction is a direction normal to the first direction.

31. The external ankle brace of claim 22, wherein the second direction is a direction of ankle dorsiflexion movement.

32. The external ankle brace of claim 22, wherein the second direction is a direction of ankle plantar flexion movement.

33. The external ankle brace as set forth in claim 22, wherein the foot section is a monolithic body made of plastic.

34. An external ankle brace, comprising:
a lower leg section configured to interface with a leg of a human at a lower leg thereof; and
a foot section configured to interface with a shoe worn on a foot of the human at locations where the foot of the human is located, wherein
the external ankle brace is configured to restrict movement of an ankle of the human in a first direction, wherein said external ankle brace is configured to be disposed on the exterior of the shoe of the human, the shoe having a heel portion, a sole, oppositely disposed sides, and a toe section, the heel portion being at a rear of the shoe, and the toe section being at a front of the shoe,
the foot section is established by a portion that includes a first subportion, a second subportion and a third subportion, the first subportion of the foot section being configured to receive the rear of the shoe, the second subportion of the foot section extending away from the first subportion and configured to be on a medial side of the foot when the brace is worn by the human, the third subportion of the foot section extending away from the first subportion and configured to be on a lateral side of the foot when the brace is worn by the human, the lower leg section includes a lateral upright extension that includes a portion that extends upward away from the foot section, the lateral upright extension being rotationally attached to the foot section,
the lower leg section includes a medial upright extension that includes a portion that extends upward away from the foot section, the medial upright extension being rotationally attached to the foot section, and
the external ankle brace further includes:
a lower fastening system comprising at least one connecting strap connecting said second subportion to said third subportion underneath the sole of the shoe;
an upper fastening system comprising at least one connecting strap connecting said second subportion to said third subportion across the top of the shoe; and
a lower leg section fastening system comprising at least one connecting strap connecting said portion of said medial upright extension that extends upwardly away from the foot section with said portion of said lateral upright extension that extends upwardly away from the foot section.

35. The external ankle brace as set forth in claim 34, wherein the external ankle brace is configured to restrict movement of an ankle of the human in a second direction.

36. The external ankle brace as set forth in claim 35, wherein the second direction is a normal direction to the first direction.

37. The external ankle brace of claim 34, wherein at least one connecting strap connects the second subportion to the third subportion underneath the sole of the shoe, and the foot fastening arrangement comprises a second connecting strap connecting the second subportion to the third subportion across the top of the shoe.

38. The external ankle brace as set forth in claim 37, wherein said lateral ankle joint in combination with said lateral upright extension and said foot section prevent movement of the ankle in the first direction.

39. The external ankle brace as set forth in claim 34, wherein the external ankle brace is configured to restrict movement of an ankle of the human in all directions.

40. The external ankle brace as set forth in claim 34, wherein the external ankle brace is configured permit movement of the ankle in a second direction and a third direction opposite the second direction, the second direction and third direction normal to the first direction.

41. The external ankle brace as set forth in claim 34, wherein the external ankle brace is configured to restrict movement of the ankle in a fourth direction opposite the first direction.

42. An external ankle brace of claim 34, wherein the brace is hingeless.

43. The external ankle brace of claim 34, wherein the external ankle brace is configured permit movement of the ankle in a second direction and a third direction opposite the second direction, wherein the second direction is a direction of ankle dorsiflexion movement, wherein the third direction is a direction of ankle plantar flexion movement.

44. The external ankle brace of claim 34, wherein the external ankle brace is configured prevent movement of the ankle in a second direction opposite the first direction, the second direction is a direction of ankle dorsiflexion movement, and the first direction is a direction of ankle plantar flexion movement.

45. An external ankle brace, comprising:
a lower leg section configured to interface with a leg of a human at a lower leg thereof; and
a foot section configured to interface with a shoe worn on a foot of the human at locations where the foot of the human is located, wherein
the external ankle brace is configured to restrict movement of an ankle of the human in a first direction and permit movement of the ankle in a second direction, wherein said external ankle brace is configured to be disposed on the exterior of the shoe of the human, the shoe having a heel portion, a sole, and a toe section, the heel portion being at a rear of the shoe, and the toe section being at a front of the shoe,
the foot section is established by a portion that includes a first subportion, a second subportion and a third subportion, the first subportion of the foot section being configured to receive the rear of the shoe, the second subportion of the foot section extending away from the first subportion and configured to be on a medial side of the foot when the brace is worn by the human, the third subportion of the foot section extending away from the first subportion and configured to be on a lateral side of the foot when the brace is worn by the human,
the lower leg section includes a lateral upright extension that includes a portion that extends upward away from the foot section, the lateral upright extension being rotationally attached to the foot section,
the lower leg section includes a medial upright extension that includes a portion that extends upward away from the foot section, the medial upright extension being rotationally attached to the foot section,
the external ankle brace further includes:
a foot fastening arrangement comprising at least one connecting strap connecting said second subportion to said third subportion; and
a lower leg section fastening system comprising at least one connecting strap connecting said portion of said medial upright extension that extends upwardly away from the foot section with said portion of said lateral upright extension that extends upwardly away from the foot section, and
the foot fastening arrangement comprises two connecting straps for connecting said third subportion to said second subportion underneath the sole of the shoe forward of the talus of the wearer's foot.

46. Footwear, comprising:
the external ankle brace of claim 1; and
the shoe, wherein
the shoe is an athletic shoe with cleats.

* * * * *